US008337202B2

(12) United States Patent
Bando et al.

(10) Patent No.: US 8,337,202 B2
(45) Date of Patent: Dec. 25, 2012

(54) APPARATUS FOR MEASURING DENTAL OCCLUSION (75) Inventors: Eiichi Bando, Tokushima (JP);
Masanori Nakano, Tokushima (JP);
Maki Hosoki, Tokushima (JP);
Motoharu Kori, Tokushima (JP); Kazuo Okura, Tokushima (JP); Yoshihiro Kubo, Tokushima (JP); Keisuke Nishigawa, Tokushima (JP); Hisahiro Takeuchi, Tokushima (JP); Yutaka Sato, Tokushima (JP)

(73) Assignees: The University of Tokushima, Tokushima (JP); Kabushikikaisha Shofu, Kyoto (JP)

( * ) Notice: Subject to any disclaimer, the term of this patent is extended or adjusted under 35 U.S.C. 154(b) by 0 days.

(21) Appl. No.: 12/812,298

(22) PCT Filed: Mar. 26, 2008

(86) PCT No.: PCT/JP2008/055788
§ 371 (c)(1),
(2), (4) Date: Nov. 15, 2010

(87) PCT Pub. No.: WO2009/087782
PCT Pub. Date: Jul. 16, 2009

(65) Prior Publication Data
US 2011/0053110 A1 Mar. 3, 2011

(30) Foreign Application Priority Data

Jan. 11, 2008 (JP) ................................. 2008-004891

(51) Int. Cl.
*A61C 19/04* (2006.01)
*A61B 5/117* (2006.01)

(52) U.S. Cl. ......................................... 433/68; 600/590

(58) Field of Classification Search .................... 433/73, 433/75, 68–71, 140; 600/589, 590
See application file for complete search history.

(56) References Cited

U.S. PATENT DOCUMENTS

| 4,521,186 | A | * | 6/1985 | Wodlinger et al. | 433/71 |
| 5,730,151 | A | * | 3/1998 | Summer et al. | 600/587 |
| 5,810,586 | A | * | 9/1998 | Fjelstad | 433/68 |
| 6,120,290 | A | * | 9/2000 | Fukushima et al. | 433/69 |
| 6,579,249 | B2 | * | 6/2003 | Kato et al. | 600/590 |
| 6,582,931 | B1 | * | 6/2003 | Kois et al. | 435/56 |
| 7,699,607 | B2 | * | 4/2010 | Margossian | 433/73 |
| 7,955,077 | B2 | * | 6/2011 | Shindo et al. | 433/68 |

FOREIGN PATENT DOCUMENTS

JP 2004229943 * 8/2004

OTHER PUBLICATIONS

International Search Report issued May 20, 2008 in International (PCT) Application No. PCT/JP2008/055788. Eiichi Bando, "Chairside Examination of Mastication and Jaw Movement", The Journal of the Japan Dental Association, 2005, vol. 57, No. 11, pp. 1159-1169.

* cited by examiner

*Primary Examiner* — Yogesh Patel
(74) *Attorney, Agent, or Firm* — Wenderoth, Lind & Ponack, LLP (57) ABSTRACT An apparatus for measuring a dental occlusion includes: a position sensor (30) for detecting a position and posture of a lower jaw (12) relative to an upper jaw (11) and; an arithmetic circuit (31) for computing a posture relative to a translation distance in a state of occlusal contact. The computation is derived from the position and posture of the lower jaw (12) relative to the upper jaw (11) detected by the position sensor (30). The apparatus also includes a display monitor (32) for displaying the posture relative to the translation distance computed by the arithmetic circuit (31).

3 Claims, 11 Drawing Sheets

APPARATUS FOR MEASURING DENTAL OCCLUSION

BACKGROUND OF THE INVENTION

1. Technical Field

The present invention relates to an apparatus for measuring a dental occlusion.

2. Description of the Related Art

The inventors developed an apparatus for measuring a movement of a lower jaw relative to an upper jaw, i.e., a jaw movement. See Japanese Patent Laid-Open Publication No. 2004-229943.

Figure 1:
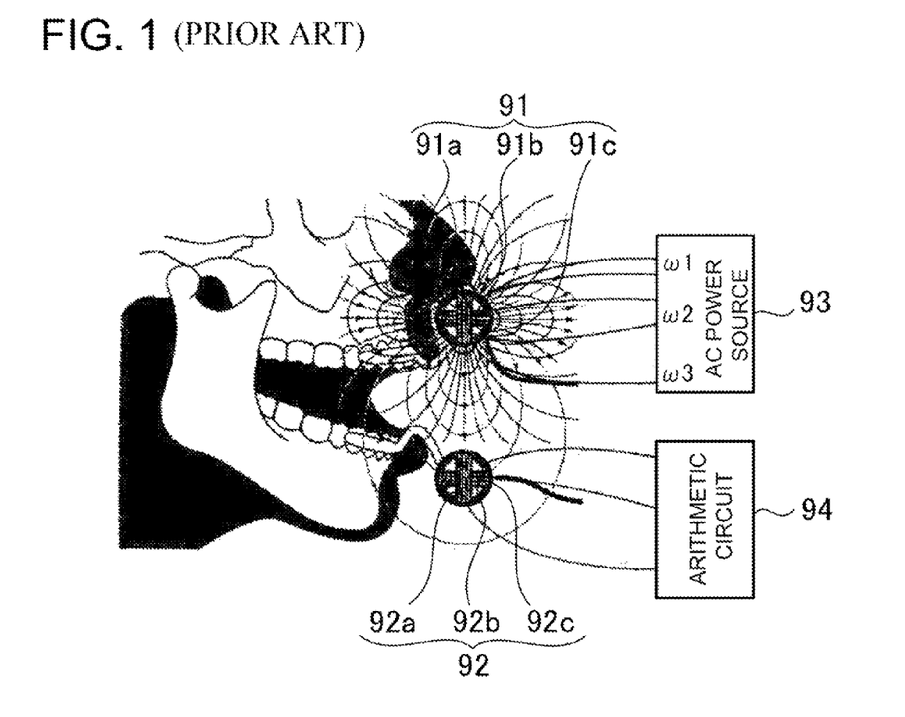
FIG. 1 is a schematic block diagram showing the apparatus for measuring the jaw movement, which was previously developed by one of the inventors.
Figure 2:
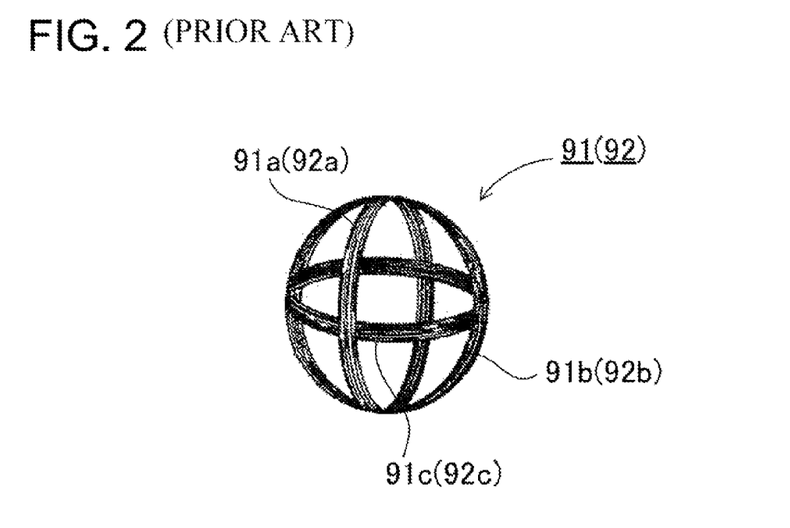
FIG. 2 is an enlarged perspective view of the exciting coil in the measuring apparatus shown in FIG. 1.

As shown in FIG. 1, the apparatus includes an exciting coil 91 rigidly coupled to the teeth on either of the upper jaw or the lower jaw; a sensor coil 92 rigidly coupled to the teeth on the jaw opposite to the jaw to which the exciting coil 91 is coupled; an AC power source 93 causing an alternating current to flow to the exciting coil 91; and an arithmetic circuit 94 computing a signal induced to the sensor coil 92 from the exciting coil 91 excited by the alternating current and detecting relative positions of the upper and lower jaws, the relative positions being derived from the position of the sensor coil 92 relative to the exciting coil 91. The exciting coil 91 and the sensor coil 92 are disposed in a mutually spaced-apart relation. As shown in FIG. 2, the exciting coil 91 and the sensor coil 92 each includes three sets of coils 91a, 91b, 91c (92a, 92b, 92c) wound in directions orthogonal to each other. In this apparatus for measuring the jaw movement, the AC power source 93 is connected to each of the coils 91a, 91b, 91c in the exciting coil 91, the alternating voltage induced to each of coils 92a, 92b, 92c in the sensor coil 92 is computed by the arithmetic circuit 94, and thus the relative positions of the lower jaw and the upper jaw are detected.

SUMMARY OF THE INVENTION

1. Problems to be Solved

The above-mentioned apparatus for measuring the jaw movement computes and displays a translation locus of the lower jaw relative to the upper jaw in a state that a closed mouth is widely opened and the lower jaw makes excursions. The apparatus for measuring the jaw movement can accurately determine the movement of the temporomandibular joint. This apparatus for measuring the jaw movement, however, can detect the state of the temporomandibular joint but cannot detect a dental occlusion. For this reason, the apparatus cannot be effectively used for making a denture.

In making a denture, it is important to measure not only an occlusion in a straight-bitten intercuspal position but also a dental articulation during excursions. This is because, when the food is actually crunched with the teeth, the teeth are not only translated up and down but also ground in a state of occlusal contact. Further, in a state that the lower jaw is translated forwardly, it is considered to be undesirable for the lower jaw to rotate in a direction of closing the mouth toward the upper jaw. Consequently, in making an ideal denture, it is important to accurately detect the state of the tooth translation during excursions.

The present invention has been made to overcome the above-mentioned disadvantage. It is an important object of the present invention to provide such an apparatus for measuring a dental occlusion as may be able to accurately detect a dental occlusion by detecting and displaying a posture and locus relative to a translation distance of the upper and lower teeth in a state of occlusal contact.

2. Means to Solve the Problems

The apparatus for measuring a dental occlusion in accordance with a first aspect of the present invention includes:

a position sensor 30 for detecting a position and posture of a lower jaw 12 relative to an upper jaw 11;

an arithmetic circuit 31 for computing an posture relative to a translation distance in a state of occlusal contact, such computation being derived from the position and posture of the lower jaw 12 relative to the upper jaw 11 detected by the position sensor 30; and a display monitor 32 for displaying the posture relative to the translation distance computed by the arithmetic circuit 31.

In the apparatus for measuring the dental occlusion in accordance with a second aspect of the present invention, the arithmetic circuit 31 computes a rotation angle relative to the translation distance in the state of occlusal contact, and the display monitor 32 displays the rotation angle relative to the translation distance.

The apparatus for measuring the dental occlusion in accordance with a third aspect of the present invention includes:

a position sensor 30 for detecting a position and posture of a lower jaw 12 relative to an upper jaw 11;

an arithmetic circuit 31 for computing a translation locus of a specific point in an occlusal plane 34 with respect to the upper jaw 11, the translation locus being relative to a translation distance in a state of occlusal contact, and such computation being derived from the position and posture of the lower jaw 12 relative to the upper jaw 11 detected by the position sensor 30; and a display monitor 32 for displaying the translation locus of the specific point in the occlusal plane 34 with respect to the translation distance computed by the arithmetic circuit 31.

In the apparatus for measuring the dental occlusion in accordance with a fourth aspect of the present invention, the arithmetic circuit 31 computes the translation locus away from an intercuspal position 33, and the display monitor 32 displays the translation locus away from the intercuspal position 33.

The apparatus for measuring a dental occlusion in accordance with a fifth aspect of the present invention, comprising:

a position sensor 30 for detecting a position and posture of a lower jaw 12 relative to an upper jaw 11;

an arithmetic circuit 31 for computing an posture relative to a translation distance in a state of occlusal contact and also computing a translation locus of a specific point in an occlusal plane 34 with respect to the upper jaw 11, the translation locus being relative to a translation distance in a state of occlusal contact, and such computation being derived from the position and posture of the lower jaw 12 relative to the upper jaw 11 detected by the position sensor 30; and a display monitor 32 for displaying the posture relative to the translation distance computed by the arithmetic circuit 31 and also displaying the translation locus of the specific point in the occlusal plane 34 with respect to the translation distance computed by the arithmetic circuit 31.

3. Effect of the Invention

A feature of the instant apparatus for measuring the dental occlusion is that a dental occlusion can be accurately detected by detecting and displaying the posture and locus relative to the translation distance in a state of occlusal contact.

In accordance with a first aspect of the present invention, the apparatus for measuring the dental occlusion computes and displays the posture relative to the translation distance in the state of occlusal contact, such computation being derived from the position and posture of the lower jaw relative to the upper jaw detected by the position sensor, and thus it becomes clear that, when the teeth are translated in the state of occlusal contact, in what posture the lower teeth will translate with respect to the upper teeth. Particularly, in accordance with a second aspect of the present invention, the apparatus for measuring the dental occlusion computes and displays the rotation angle relative to the translation distance, and thus it becomes clear that, when the teeth are translated in the state of occlusal contact, in what inclination the lower teeth will translate with respect to the upper teeth.

Further, in accordance with a third aspect of the present invention, the apparatus for measuring the dental occlusion computes and displays the translation locus of a specific point in an occlusal plane with respect to the upper jaw, the translation locus being relative to a translation distance in the state of occlusal contact, and such computation being derived from the position and posture of the lower jaw relative to the upper jaw detected by the position sensor, and thus it becomes clear that, when the teeth are translated in the state of occlusal contact, in what manner the specific point of the lower teeth will translate with respect to the upper teeth. Particularly, in accordance with a fourth aspect of the present invention, the apparatus for measuring the dental occlusion computes and displays the translation locus away from the intercuspal position, and thus it becomes clear that, when the teeth are translated in the state of occlusal contact, in what manner the lower teeth will translate with respect to the intercuspal position.

Furthermore, in accordance with a fifth aspect of the present invention, the apparatus for measuring the dental occlusion computes and displays the posture relative to the translation distance in a state of occlusal contact and also computes and displays the translation locus of the specific point in an occlusal plane with respect to the upper jaw, the translation locus being relative to the translation distance in the state of occlusal contact, and such computation being derived from the position and posture of the lower jaw relative to the upper jaw detected by the position sensor; and thus it becomes clear that, when the teeth are translated in the state of occlusal contact, in what posture and manner the lower teeth will translate with respect to the upper teeth.

DESCRIPTION OF REFERENCE NUMERALS

1 . . . Exciting Coil
1a . . . X-axis Coil
1b . . . Y-axis Coil
1c . . . Z-axis Coil
2 . . . Sensor Coil
2a . . . X-axis Coil
2b . . . Y-axis Coil
2c . . . Z-axis Coil
3 . . . AC Power Source
4 . . . Detection Circuit
5 . . . Fixture
6 . . . Fixture
7 . . . Core Material
7A . . . Plane
7B . . . Recess
8 . . . Loop Coil
9 . . . Core
10 . . . Sheet Material
11 . . . Upper Jaw
12 . . . Lower Jaw
20 . . . Fixation Assembly
20A . . . Back Side Wall
20B . . . Right Side Wall
20C . . . Top Side Plate
21 . . . Head Fixation Mechanism
30 . . . Position Sensor
31 . . . Arithmetic Circuit
32 . . . Display Monitor
33 . . . Intercuspal Position
34 . . . Occlusal Plane
91 . . . Exciting Coil
91a . . . Coil
91b . . . Coil
91c . . . Coil
92 . . . Sensor Coil
92a . . . Coil
92b . . . Coil
92c . . . Coil
93 . . . AC Power Source
94 . . . Arithmetic Circuit

DETAILED DESCRIPTION OF THE INVENTION

Embodiments in accordance with the present invention shall be described hereinafter in conjunction with the accompanying drawings. It should be noted, however, that the ensuing description of embodiments is merely illustrative of the apparatus for measuring the dental occlusion only to embody technical ideas conceived in the present invention and that the invention shall in no way be specifically limited to the apparatus for measuring the dental occlusion as described below.

Further, in the present disclosure, for the purpose of better understanding the scope of the claims, the numerals corresponding with the members described in the embodiments are affixed to the members described in the "Claims" and the "Means to Solve the Problems". It should be noted that the members described in the scope of claims are in no way limited to the members described in the embodiments.

Figure 3:
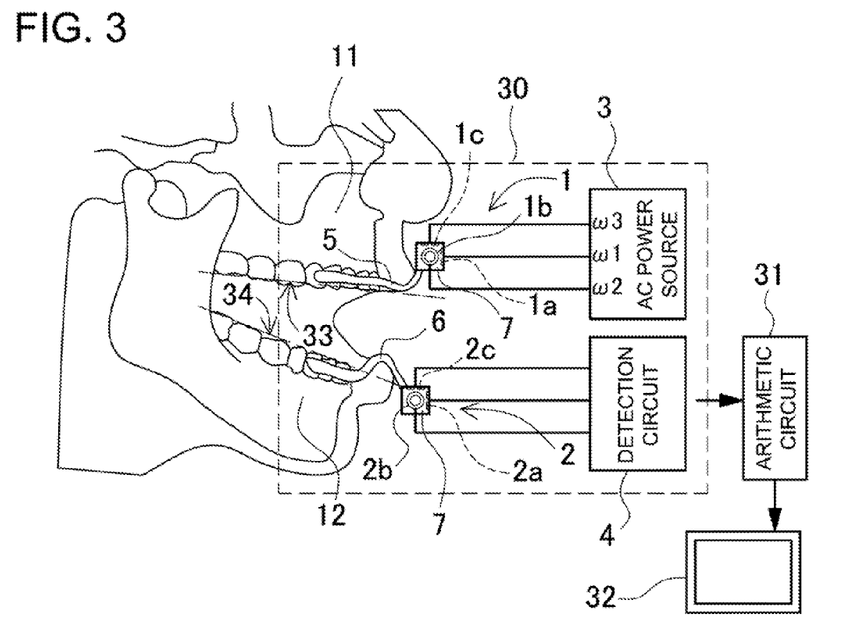
FIG. 3 is a schematic block diagram showing an apparatus for measuring the dental occlusion in accordance with an embodiment of the present invention.

The apparatus for measuring the dental occlusion as shown in FIG. 3 includes: a position sensor 30 for detecting a position and posture of a lower jaw relative to an upper jaw; an arithmetic circuit 31 for computing an posture relative to a translation distance in a state of occlusal contact or for computing a translation locus of a specific point in an occlusal plane 34 with respect to the upper jaw 11, the translation locus being relative to the translation distance, and such computation being derived from the position and posture of the lower jaw relative to the upper jaw detected by the position sensor 30; and a display monitor 32 for displaying the posture relative to the translation distance computed by the arithmetic circuit 31.

The feature of the instant apparatus for measuring the dental occlusion is that either the posture relative to the translation distance in the state of occlusal contact or the translation locus of the specific point in the occlusal plane with respect to the upper jaw is computed and displayed, such computation being derived from the position and posture of the lower jaw relative to the upper jaw detected by the position sensor. In the present invention, therefore, the position sensor for detecting the position and posture of the lower jaw relative to the upper jaw is not specifically limited to the structure as will be described below. The position sensor can be of any type of position sensor for measuring the jaw movement as is currently used or may be made available in the future.

The position sensor 30 detects the position and posture of the lower jaw 12 relative to the upper jaw 11. The position sensor 30, setting the intercuspal position 33 as a reference, detects the position and posture of the lower jaw 12 relative to the upper jaw 11. With this intercuspal position 33 as a reference point, the position sensor 30 detects the translation distance of the lower jaw 12 each in terms of X-axis, Y-axis, and Z-axis and also detects the rotation angle each about the X-axis, Y-axis, and Z-axis. The position sensor 30 can respectively be structured as shown in FIG. 3 through FIG. 9. Each of the position sensors 30 shown in these drawings includes an exciting coil 1 and a sensor coil 2 rigidly coupled to the teeth on the upper and lower jaws respectively; an AC power source 3 for causing the AC current to flow to the exciting coil 1; and a detection circuit 4 for detecting a position of the lower jaw 12 relative to the upper jaw 11, the position being derived from a position of the sensor coil 2 relative to the exciting coil 1 by computing a signal induced to the sensor coil 2 from the exciting coil 1 excited by the alternating current. In the position sensor 30 shown in FIG. 3, the exciting coil 1 is rigidly coupled to the teeth on the upper jaw 11, while the sensor coil 2 is rigidly coupled to the teeth on the lower jaw 12. In this position sensor, however, the sensor coil can also be rigidly coupled to the teeth on the upper jaw, with the exciting coil being rigidly coupled to the teeth on the lower jaw. The exciting coil 1 and the sensor coil 2 are rigidly coupled to the teeth on the jaws respectively via fixtures 5, 6. However, the exciting coil and the sensor coil can also be fixed to the gums respectively via the fixtures. It should be added here that the "tooth" or "teeth" has a wider meaning which includes a denture as well.

Figure 4:
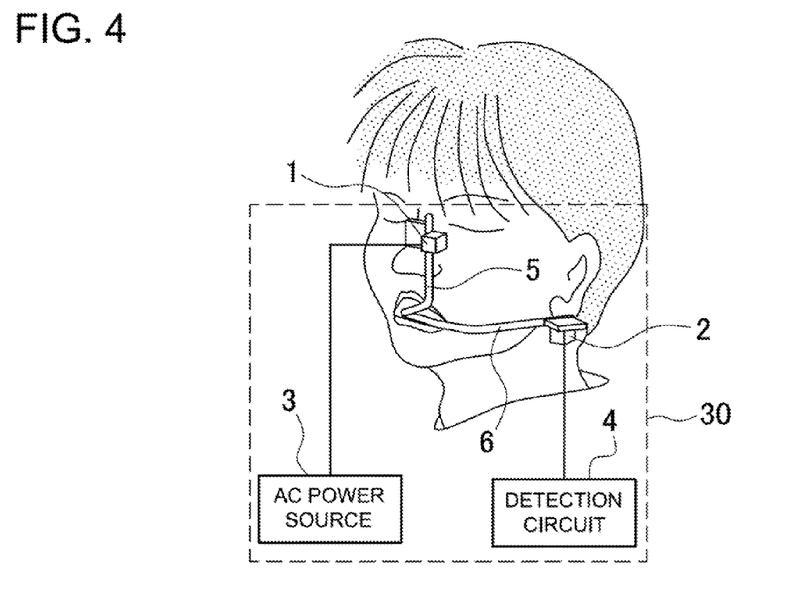
FIG. 4 is a schematic perspective view showing the state that the patient is mounted with the position sensor in the measuring apparatus shown in FIG. 3.
Figure 5:
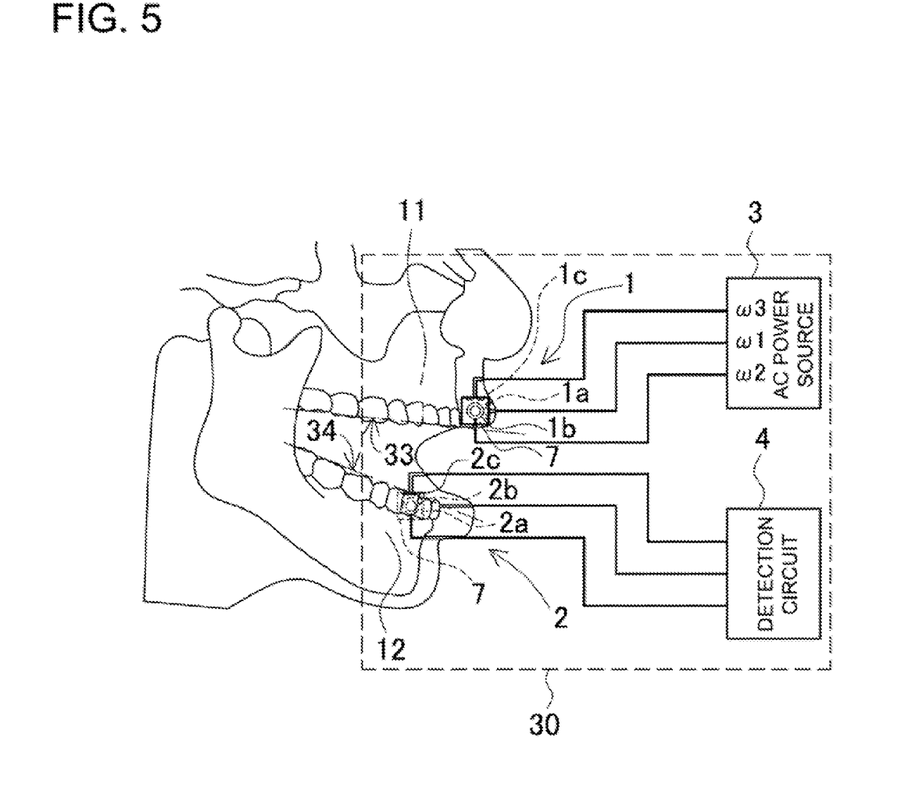
FIG. 5 is a schematic block diagram showing another example of the position sensor.

FIG. 4 illustrates a state that the position sensor 30 shown in FIG. 3 is mounted to a patient. In this illustrated position sensor 30, the exciting coil 1 is disposed forwardly of the upper jaw 11 via the fixture 5 on the upper jaw 11, while the sensor coil 2 is disposed outwardly of a cheek via the fixture 6 on the lower jaw 12. In the position sensor, however, the exciting coil can also be disposed outwardly of the cheek, with the sensor coil being disposed forwardly of the upper jaw. Further, in the position sensor, the exciting coil and the sensor coil do not necessarily have to be disposed in such positions as mentioned above, and so the sensors may be slightly offset from the above-mentioned positions or alternatively the sensors may be disposed in positions opposite to each other. For example, in the position sensor 30 as shown in FIG. 5, both of the exciting coil 1 and the sensor coil 2 can be disposed within the mouth cavity as well. Such intraorally disposed exciting coil 1 and sensor coil 2 can be directly fixed to the teeth so as to be rigidly coupled to the upper jaw 11 or the lower jaw 12. The exciting coil 1 and sensor coil 2 shown in FIG. 5 are rigidly coupled to the surfaces of the teeth in direct adhesion. In particular, the intraorally disposed exciting coil 1 and sensor coil 2 are preferably disposed inside or outside the anterior teeth in order to facilitate measuring the upper and lower jaw movement. In the position sensor 30 shown in FIG. 5, the exciting coil 1 is rigidly coupled directly to the outside of the anterior teeth on the upper jaw 11, with the sensor coil 2 being rigidly coupled directly to the inside of the anterior teeth on the lower jaw 12. In the position sensor 30 shown in FIG. 5, both of the exciting coil 1 and the sensor coil 2 are disposed within the mouth cavity, but only one of the exciting coil or the sensor coil may be disposed within the mouth cavity.

Figure 6:
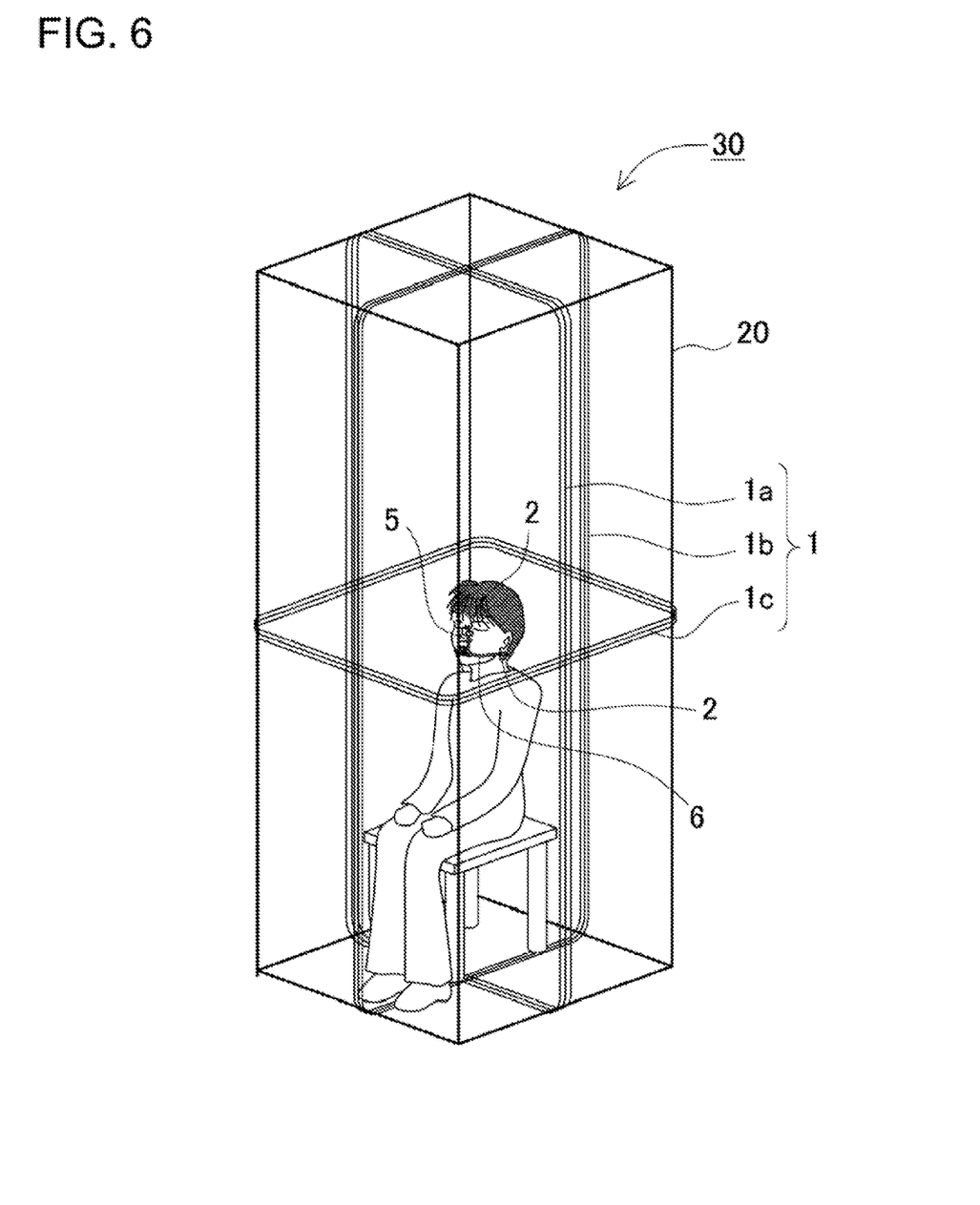
FIG. 6 is a schematic block diagram showing yet another example of the position sensor.
Figure 7:
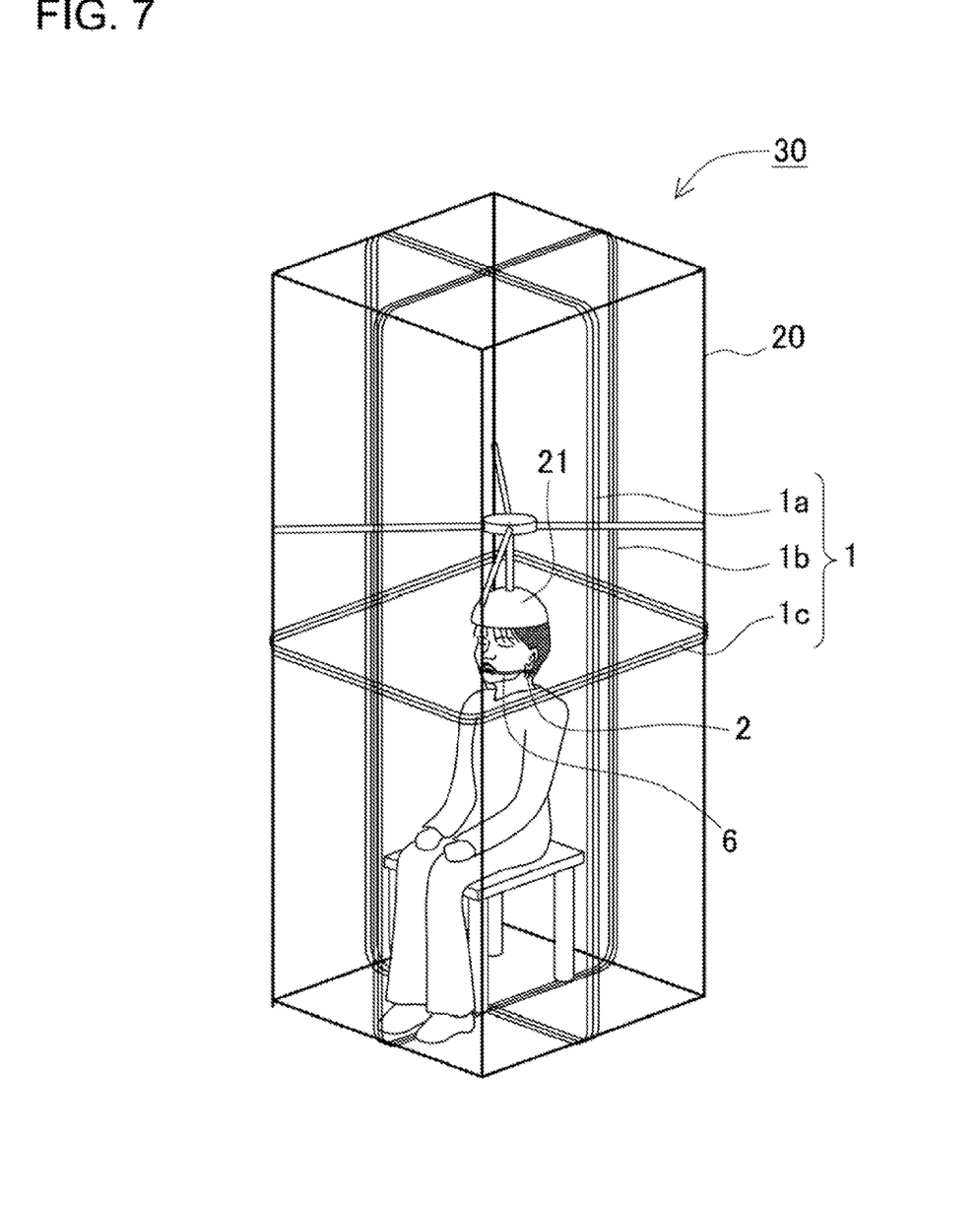
FIG. 7 is a schematic block diagram showing even another example of the position sensor.

Further, it is also possible to detect the relative positions of the lower jaw 12 and the upper jaw 11 in terms of X-axis, Y-axis, and Z-axis by disposing the exciting coil 1 outside the patient and rigidly coupling the sensor coil 2 to both the upper jaw 11 and the lower jaw 12 as shown in FIG. 6 or alternatively by fixing the patient so that he or she may not move relatively to the exciting coil 1 and rigidly coupling the sensor coil 2 to the lower jaw 12 as shown in FIG. 7. The position sensor 30 shown in FIG. 6 is provided with a fixation assembly 20 for fixing the exciting coil 1 outside the patient; the patient with the sensor coils 2 each being rigidly coupled to the teeth on the upper jaw 11 and the lower jaw 12 is placed in a fixed position inside the fixation assembly 20, so that the position of the teeth is detected by detecting the positions of the teeth on the upper jaw 11 and the lower jaw 12 relative to the fixation assembly 20. Further, in the position sensor 30 shown in FIG. 7, the fixation assembly 20 is provided with a head fixation mechanism 21 for fixing the patient's head in a fixed position. In this position sensor 30, the patient's head is fixed via the head fixation mechanism 21 in a fixed position within the fixation assembly 20 to which the exciting coil 1 is fixed, and the sensor coil 2 is rigidly coupled to the patient's lower jaw 12. This position sensor 30 detects the position of the teeth on the lower jaw 12 relative to the fixation assembly 20 to which the patient's head is fixed.

Figure 8:
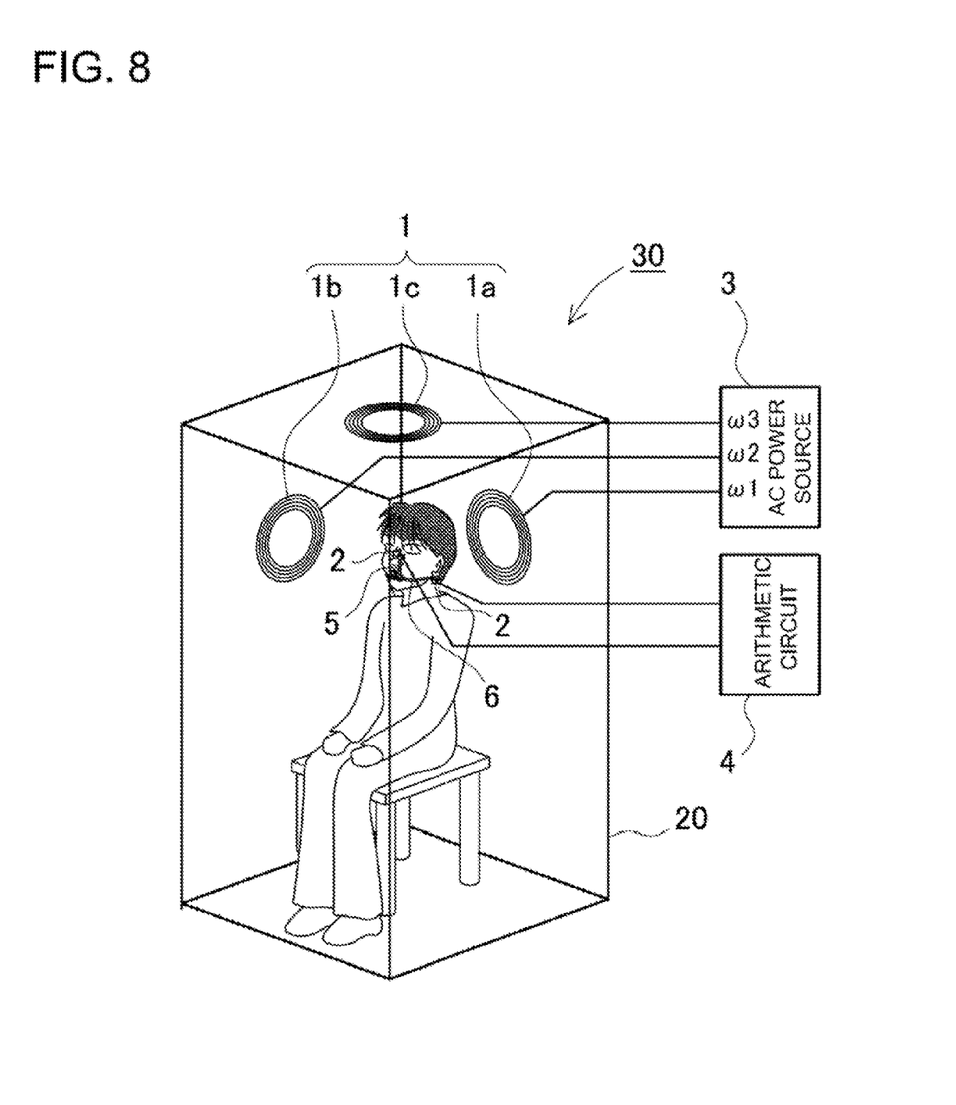
FIG. 8 is a schematic block diagram showing a further example of the position sensor.
Figure 9:
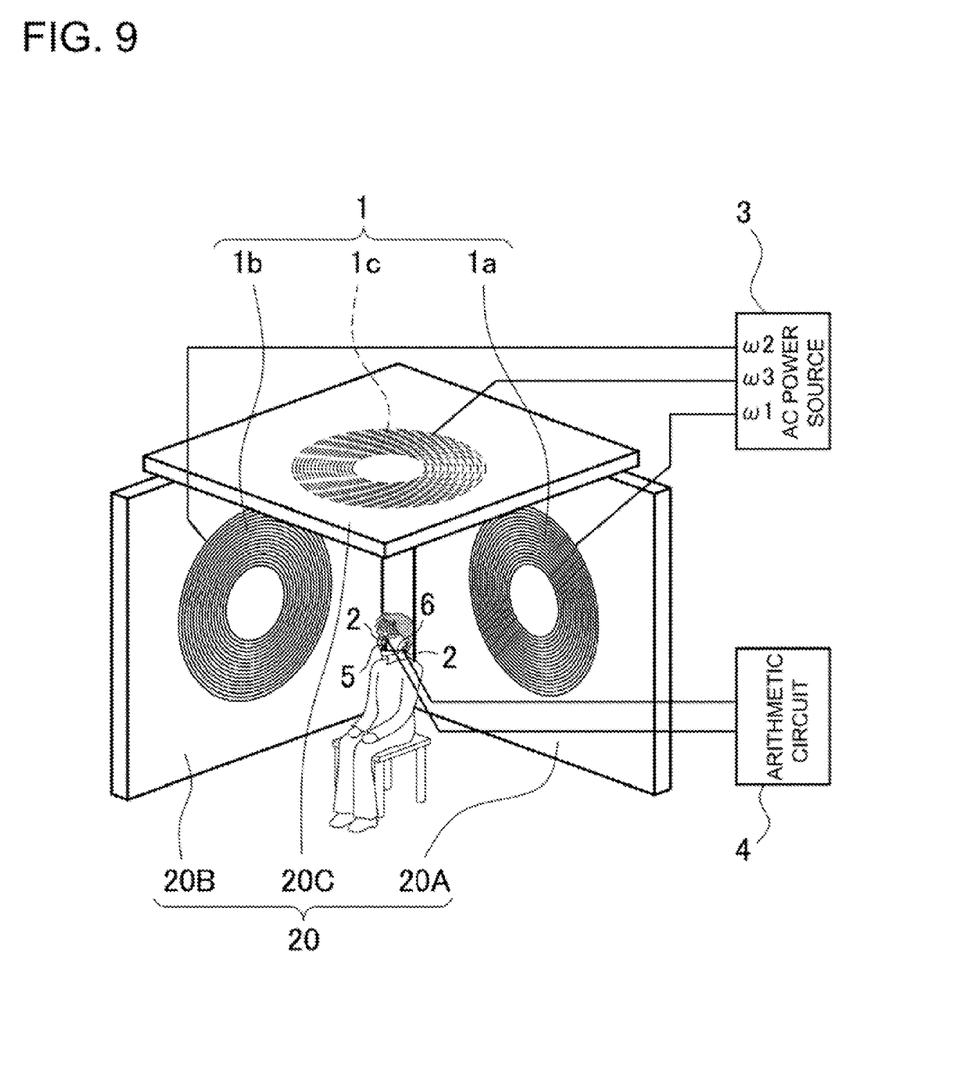
FIG. 9 is a schematic block diagram showing an alternative example of the position sensor.

Further, as can be seen in FIG. 8 and FIG. 9, the exciting coils 1 placed outside the patient can be disposed in a mutually orthogonal relationship so that each coil's central axis may be positioned in the X-axis, Y-axis, and Z-axis respectively. In the exciting coil 1 as shown in these drawings, a circular coreless coil each is disposed on the rearward surface, right side surface, and the top side surface away from the patient, constituting an X-axis coil 1a, a Y-axis coil 1b, and a Z-axis coil 1c respectively. The exciting coil 1 shown in FIG. 8 is so arranged that the X-axis coil 1a, Y-axis coil 1b, and Z-axis coil 1c are fixed on a back plane, side plane, and ceiling plane of a rectangular box being the fixation assembly 20, with each coil's central axis being positioned in the X-axis, Y-axis, and Z-axis respectively. In the case of the exciting coil 1 shown in FIG. 9, on the other hand, the X-axis coil 1a, Y-axis coil 1b, and Z-axis coil 1c are fixed on the surface of the back side wall 20A, right side wall 20B, and upper top side plate 20C, constituting the fixation assembly 20, away from the patient, with each coil's central axis being positioned in the X-axis, Y-axis, and Z-axis respectively. A feature of this structure is that a winding diameter of the exciting coil 1 can be made larger, an induction can be increased, and so a magnetic field intensity generated from the exciting coil 1 can be increased. In the exciting coil 1 shown in FIG. 9, the three fixation plates on the back side, right side, and upper side away from the patient are disposed in a mutually orthogonal relationship, constituting the fixation assembly 20. In this type of exciting coil 1, the large fixation assembly 20 can be disassembled into each fixation plate to be carried and moved away. In this exciting coil, however, it is also possible that a side wall and ceiling of a measurement chamber are used as a fixation assembly, upon which surface the X-axis coil, Y-axis coil, and Z-axis coil are fixed respectively.

The position sensor 30 shown in FIG. 8 and FIG. 9 respectively detects the position of the teeth by disposing the patient, with the sensor coils 2 being rigidly coupled to the teeth on the upper jaw 11 and lower jaw 12, in a fixed position inside the fixation assembly 20 and detecting the positions of the teeth on the upper jaw 11 and lower jaw 12 relative to the fixation assembly 20. In this position sensor, however, the position of the teeth on the lower jaw relative to the fixation assembly can also be detected by placing the patient, with the sensor coil being rigidly coupled to the teeth on the lower jaw, in a fixed position inside the fixation assembly and fixing the patient's head to the fixation assembly via the head fixation mechanism.

In the position sensor 30 shown respectively in FIG. 6 through FIG. 9, the exciting coil 1 is disposed such that the X-axis coil 1a, Y-axis coil 1b, and Z-axis coil 1c are in a relationship that the respective central axis is orthogonal to each other. The position sensor can, however, measure the patient's jaw movement even if each central axis of the X-axis coil, Y-axis coil, and Z-axis coil in the exciting coil is in a relationship being slightly offset from the mutually orthogonal relationship. Further, in the position sensor 30 shown respectively in FIG. 6 through FIG. 9, the exciting coil 1 is disposed such that the central axes of the X-axis coil 1a, Y-axis coil 1b, and Z-axis coil 1c intersect at one common point. In these position sensors 30, the patient is placed inside the fixation assembly 20 such that the sensor coil 2 is positioned in the vicinity of the cross point of the central axes of the exciting coil 1, so that the jaw movement may be measured as ideally as possible. The position sensor can, however, measure the patient's jaw movement even if the sensor coil is slightly offset from the cross point of the central axes of the exciting coil.

Figure 10:
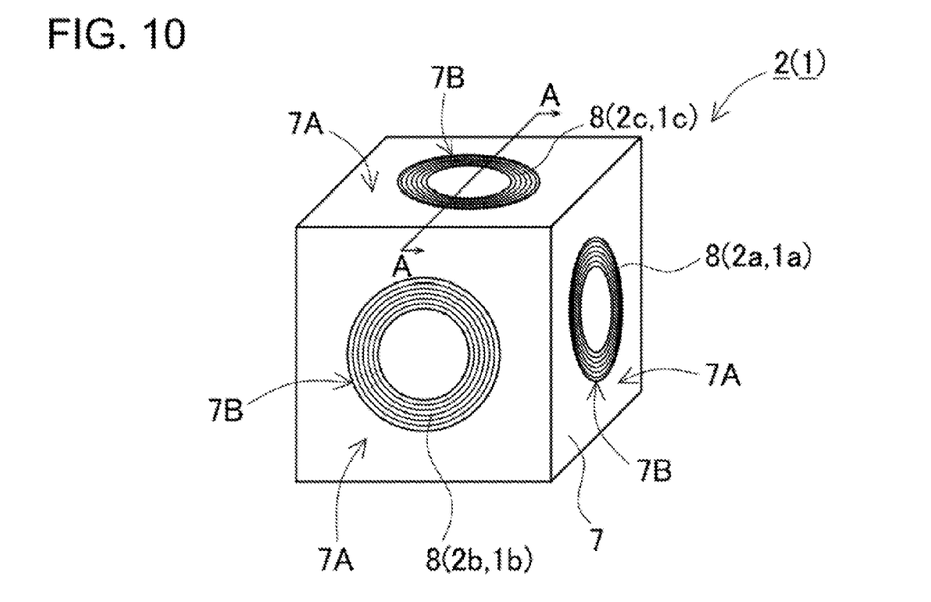
FIG. 10 is an enlarged perspective view showing an example of the sensor coil.
Figure 11:
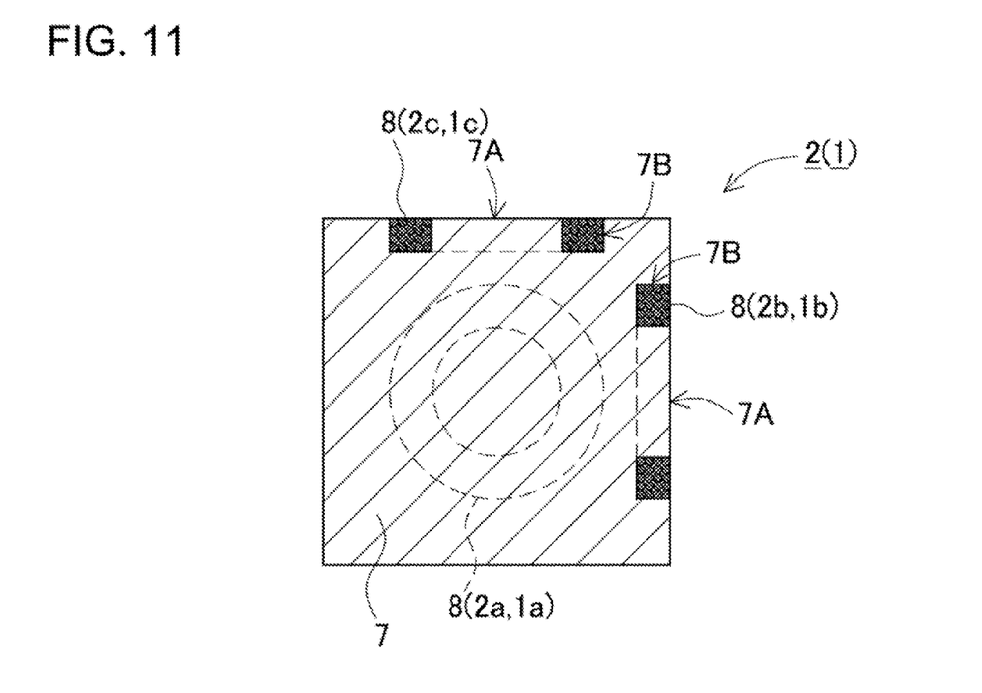
FIG. 11 is a cross-sectional view of the sensor coil shown in FIG. 10 and taken along lines A-A.

In the position sensors 30 shown in FIG. 3 through FIG. 5, an identical type is used for the sensor coil 2 and the exciting coil 1. In these position sensors 30, the identical coil can be produced and used for the exciting coil 1 and the sensor coil 2. For this reason, a mass production becomes possible with efficiency and at a less expensive cost. Further, the sensor coil and the exciting coil can be optimized by varying the winding diameters and the wire turns. For example, it is also possible to use a larger gauge of wire in the exciting coil to allow a stronger current to flow through and to use a smaller gauge of wire and a larger number of wire turns in the sensor coil to enhance sensitivity. As shown in FIG. 10 and FIG. 11, these sensor coils 2 and exciting coils 1 respectively include the X-axis coil 2a, 1a, the Y-axis coil 2b, 1b, and the Z-axis coil 2c, 1c, which are wound in a mutually orthogonal direction.

Figure 12:
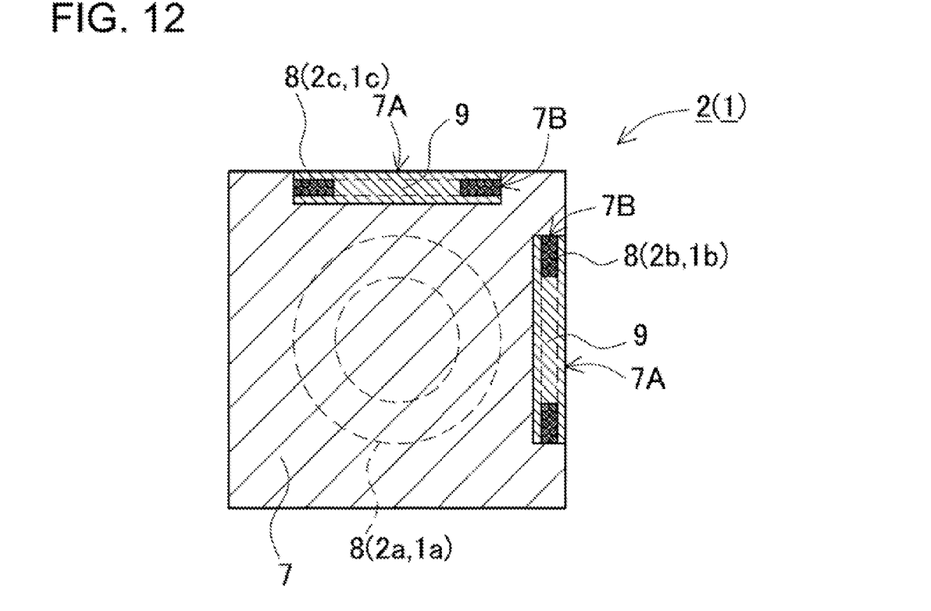
FIG. 12 is a cross-sectional view showing another example of the sensor coil.

The X-axis coils 2a, 1a, the Y-axis coils 2b, 1b, and the Z-axis coils 2c, 1c are respectively composed of a loop coil 8 wound circularly by a coil winding machine, and the loop coil 8 is fixed on the surface of a core material to make up the sensor coil 2 and the exciting coil 1. The sensor coil 2 shown in FIG. 6 through FIG. 9 is also of the same structure as the sensor coil 2 shown in FIG. 10 and FIG. 11. The position sensor can, however, measure the patient's jaw movement even if the X-axis coil, Y-axis coil, and Z-axis coil of the exciting coil and the sensor coil are in a relationship being slightly offset from the mutually orthogonal relationship. The loop coil 8 is produced by adhesively fixing the electrically conductive wire, with its electrically insulated surface, which is wound multiple times into a circular form. The loop coil does not necessarily have to be wound into a circular form but can be wound multiple times, for example, into a polygonal form and then fixed adhesively. Further, as shown in FIG. 12, the loop coil 8 can also be produced by being wound around the periphery of a core 9 made of a magnetic material.

An inductance of the X-axis coils 2a, 1a, the Y-axis coils 2b, 1b, and the Z-axis coils 2c, 1c is specifically determined in accordance with the number of wire turns and the winding diameters in the coil 8. In the X-axis coils 2a, 1a, the Y-axis coils 2b, 1b, and the Z-axis coils 2c, 1c, the inductance can be made larger by increasing the number of wire turns and the winding diameter in the loop coil 8. The loop coil 8 of the exciting coil 1 determines the magnetic field intensity generated by the inductance; the larger the inductance, the stronger the magnetic field intensity generated from the X-axis coil 1a, the Y-axis coil 1b, and the Z-axis coil 1c. The exciting coil 1 with a larger inductance increases the magnetic field intensity and also increases the AC voltage induced to the sensor coil 2. The loop coil 8 of the sensor coil 2 increases the inductance and thus elevates the voltage level of the AC signal induced to the X-axis coil 2a, the Y-axis coil 2b, and the Z-axis coil 2c. When the voltage level of the AC signal induced to the sensor coil 2 is elevated, the accuracy of measurement can be enhanced in detecting the position of the sensor coil 2. Therefore, an increased inductance of the loop coil 8 used as the X-axis coil 2a, the Y-axis coil 2b, and the Z-axis coil 2c is effective in enhancing the accuracy of measurement.

However, the increasing of the loop coil inductance means a larger and heavier loop coil. It is better to have a smaller and lighter sensor coil and exciting coil. This is because the coils can be readily mounted to the patient and such coil-mounted patient can manage a free jaw movement. Especially, as shown in FIG. 5, it is important to specifically make smaller the sensor coil 2 and the exciting coil 1 which are adhered directly to the surface of teeth in the patient's mouth cavity and rigidly coupled to the upper jaw 11 and the lower jaw 12. Therefore, an optimal value is set for the loop coil inductance, namely the number of wire turns and the winding diameter, taking into account the position where the sensor coil and the exciting coil are rigidly coupled, the accuracy of measurement, etc. As an exemplary case of the loop coil 8 of the sensor coil 2 and exciting coil 1 to be fixed within the mouth cavity, the winding diameter is set to be 10 mm or less, and preferably 5 mm or less, while the inductance is set to be about 200 μH or more, and preferably 500 μH or more.

A core material 7 has three planes orthogonal to each other, fixing the loop coil 8 on the three planes 7A and being provided with the X-axis coil 2a, 1a, the Y-axis coil 2b, 1b, and the Z-axis coil 2c, 1c which are orthogonal to each other. The core material 7 shown in FIG. 10 is of a rectangular parallelepiped, and the loop coils 8 each is fixed on the three planes 7A of the rectangular parallelepiped which are orthogonal to each other. In order to fasten the loop coil 8 in a fixed position, the core material 7 is defined with a recess 7B to allow the loop coil 8 to be placed on the plane as shown in the cross-sectional view of FIG. 11. The recess 7B has its internal form to match with an external form of the loop coil 8, where the loop coil 8 is fitted in to be fastened in a fixed position. Further, the depth of the recess can be so structured as to be deeper than the thickness of the loop coil so that the loop coil placed in the recess may not project from the core material. The core material having the loop coil placed in the recess and prevented from projecting can be so structured as to protect the loop coil when the loop coil is contained and coated on its top surface.

The sensor coil 2 and the exciting coil 1, where the loop coil 8 serving as the X-axis coil 2a, 1a, the Y-axis coil 2b, 1b, and the Z-axis coil 2c, 1c is fixed on the parallelepiped core material 7, has the core material made of a magnetic material, and such core material 7 can increase the inductance of the loop coil 8. However, the core material does not necessarily have to be of a magnetic material, but can also use a nonmagnetic material such as a plastic material, etc., and thus a coreless coil can also be used for the loop coil.

Further, as shown in FIG. 12, when the internal form of the recess 7B provided on the plane is shaped to allow the core 9 to be fitted in, the loop coil 8 wound around the core 9 can be placed in a fixed position.

Figure 13:
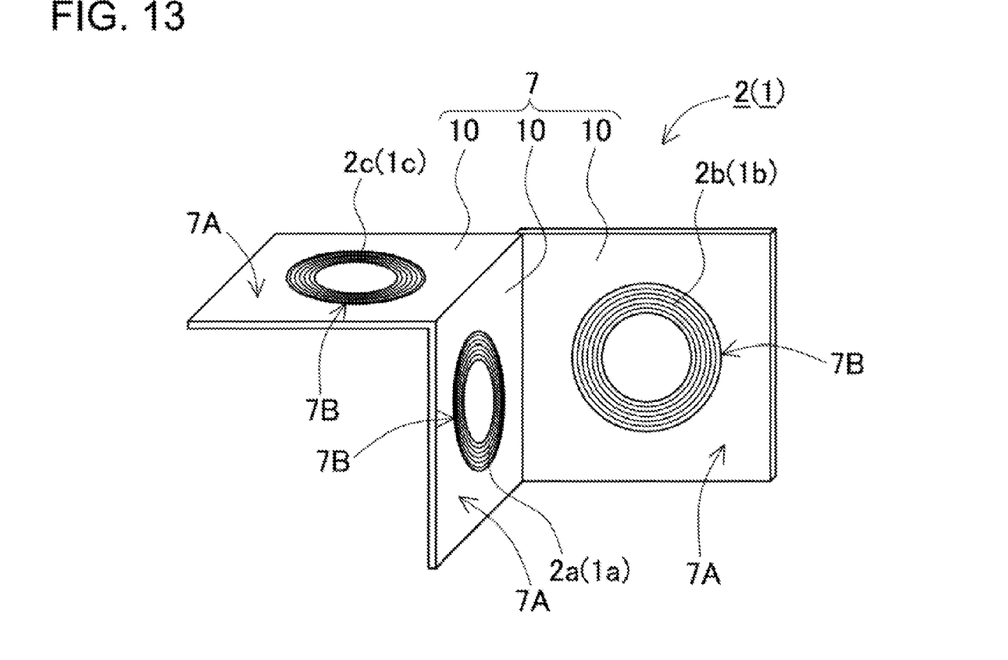
FIG. 13 is a perspective view showing even another example of the sensor coil.

Further, in the core material 7 shown in FIG. 13, the planes 7A orthogonal to each other are placed laterally along X-axis, and the loop coil 8 is fixed on the plane. In this illustrated core material 7, three sheet materials 10 are interconnected to be mutually orthogonal. In this core material 7, when viewed from left to right in the drawing, the loop coils 8 being the Z-axis coil 2c, 1c, the X-axis coil 2a, 1a, and the Y-axis coil 2b, 1b are fixed to the core material 7. In this core material 7 as well, a recess 7B can be defined in the portion of fixing the loop coil 8, and thus the loop coil 8 can be put into the recess 7B and placed in a fixed position.

The AC power source 3 excites, with the alternating currents having differing frequencies, the X-axis coil 1a, the Y-axis coil 1b, and the Z-axis coil 1c in the exciting coil 1. The AC power source 3 incorporates an oscillation means for exciting the X-axis coil 1a at an angular speed or frequency of $\omega 1$, the Y-axis coil 1b at $\omega 2$, and the Z-axis coil 1c at $\omega 3$. The AC power source 3 is capable of generating the alternating currents having differing frequencies by using a plurality of oscillation circuits, but it is also capable of producing sine waves having differing frequencies by using a microcomputer and a D/A converter. In this AC power source, a digital quantity of sine wave is produced by the microcomputer and is converted into an analog quantity by the D/A converter.

Based on the alternating voltage induced to the X-axis coil 2a, the Y-axis coil 2b, and the Z-axis coil 2c in the sensor coil 2, the detection circuit 4 computes the relative position and posture of the exciting coil 1 and the sensor coil 2, namely the relative position and posture of the upper jaw 11 and the lower jaw 12 to which the exciting coil 1 and the sensor coil 2 are rigidly coupled respectively. Based on the amplitude of the AC signal induced to the X-axis coil 2a, the Y-axis coil 2b, and the Z-axis coil 2c in the sensor coil 2, the detection circuit 4 computes the distance and posture of the sensor coil 2 relative to the exciting coil 1. This is possible because as the sensor coil 2 leaves away from the exciting coil 1, the amplitude of the alternating voltage induced to the X-axis coil 2a, the Y-axis coil 2b, and the Z-axis coil 2c in the sensor coil 2 becomes smaller, and thus being based on the posture of the sensor coil 2 relative to the exciting coil 1, the amplitude ratio of the alternating voltage induced to each of the X-axis coil 2a, the Y-axis coil 2b, and the Z-axis coil 2c varies. Therefore, based on the magnitude of the amplitude of the AC signal induced to each of the X-axis coil 2a, the Y-axis coil 2b, and the Z-axis coil 2c in the sensor coil 2, the detection circuit 4 can compute the position and posture of the sensor coil 2 relative to the exciting coil 1.

The detection circuit 4 calibrates the relative position and posture of the sensor coil 2 and the exciting coil 1, stores such calibrated result in a memory circuit, and computes the positions of the sensor coil 2 and the exciting coil 1, based on the calibrated result in storage. In this detection circuit 4, the sensor coil 2 is gradually separated away from the exciting coil 1 to change the relative position, the posture of the sensor coil 2 relative to the exciting coil 1 is changed in each relative position, and in each relative position and relative posture the amplitude of the alternating voltage induced to each X-axis coil 2a, the Y-axis coil 2b, and the Z-axis coil 2c in the sensor coil 2 is stored in the memory circuit as the calibrated data. Based on such calibrated data, and also based on the amplitude of the AC signal induced to each X-axis coil 2a, the Y-axis coil 2b, and the Z-axis coil 2c in sensor coil 2, the relative position and posture of the sensor coil 2 and the exciting coil 1 are computed. Further, when the amplitude of the alternating voltage which is not stored in the calibrated data is detected, the detection circuit 4 interpolates the calibrated data having been in storage and detects the position and posture of the sensor coil 2 relative to the exciting coil 1.

Although not shown, the detection circuit 4 includes: an amplifier for amplifying at a certain amplification factor an AC signal induced to each X-axis coil 2a, the Y-axis coil 2b, and the Z-axis coil 2c in sensor coil 2; an A/D converter for converting to a digital signal an analog signal fed out of the amplifier; a computing unit for computing the signal having been converted to a digital value by the A/D converter; and a memory circuit for storing a calibrated data. The memory circuit changes the relative positions of the exciting coil 1 and the sensor coil 2, changes the relative posture in each relative position, detects the amplitude of the alternating voltage induced to the X-axis coil 2a, the Y-axis coil 2b, and the Z-axis coil 2c, and stores such detected result as the calibrated data.

In this detection circuit 4, the alternating voltage induced to the X-axis coil 2a, the Y-axis coil 2b, and the Z-axis coil 2c in the sensor coil 2 is amplified to a predetermined amplitude by the amplifier; the amplified analog signal is converted to the digital value by the A/D converter; the relative position and posture of the exciting coil 1 and the sensor coil 2 are specifically determined from the closest calibrated data when the computing unit compares the converted digital value with the calibrated data having been stored in the memory circuit, or the calibrated data is interpolated and the relative position and the relative posture are computed. Based on the calibrated data having been stored in the memory circuit, the position sensor 30 computes the relative position and posture of the exciting coil 1 and the sensor coil 2. While correcting the measurement deviation in the exciting coil 1 and the sensor coil 2, that is, correcting the dimensional error, formation error, positional error and other factors in the exciting coil 1 and the sensor coil 2 during their production process, the position sensor 30 is capable of detecting, with very high accuracy, the relative position and posture of the exciting coil 1 and the sensor coil 2, that is, the relative position and posture of the upper jaw 11 and the lower jaw 12.

Further, without being based on the calibrated data, the detection circuit 4 can also compute the relative position and posture of the sensor coil 2 and the exciting coil 1 out of the Fourier series into which the alternating voltage induced to the X-axis coil 2a, the Y-axis 2b, and the Z-axis coil 2c in the sensor coil 2 are expanded by the use of mathematical technique such as the FFT. This position sensor 30 can detect the relative position and posture of the exciting coil 1 and the sensor coil 2 without calibration. It is also possible to detect the relative position and posture at higher accuracy by computing the relative position and posture of the exciting coil 1 and the sensor coil 2 by means of both of the calibrated data and the mathematical technique.

Based on the relative position and posture detected by the position sensor 30, the arithmetic circuit 31 computes the posture relative to the translation distance in a state of the occlusal contact. For example, with the intercuspal position as a reference, in the state of occlusal contact, when the lower teeth is translated forwardly of the upper teeth, the posture relative to the translation distance is computed, or alternatively when the lower teeth is translated laterally of the upper teeth, the posture relative to the translation distance is computed. For example, setting the frontal direction of the teeth to be the X-axis direction, the lateral direction to be the Y-axis direction, and the vertical direction of the teeth to be the Z-axis direction, the translation distance of the lower teeth relative to the upper teeth is detected. Also as a rotation angle centered about the X-axis, the Y-axis, and the Z-axis, the rotation angle relative to the translation distance is detected, in rotation about the X-axis, the Y-axis, and the Z-axis.

Figure 14:
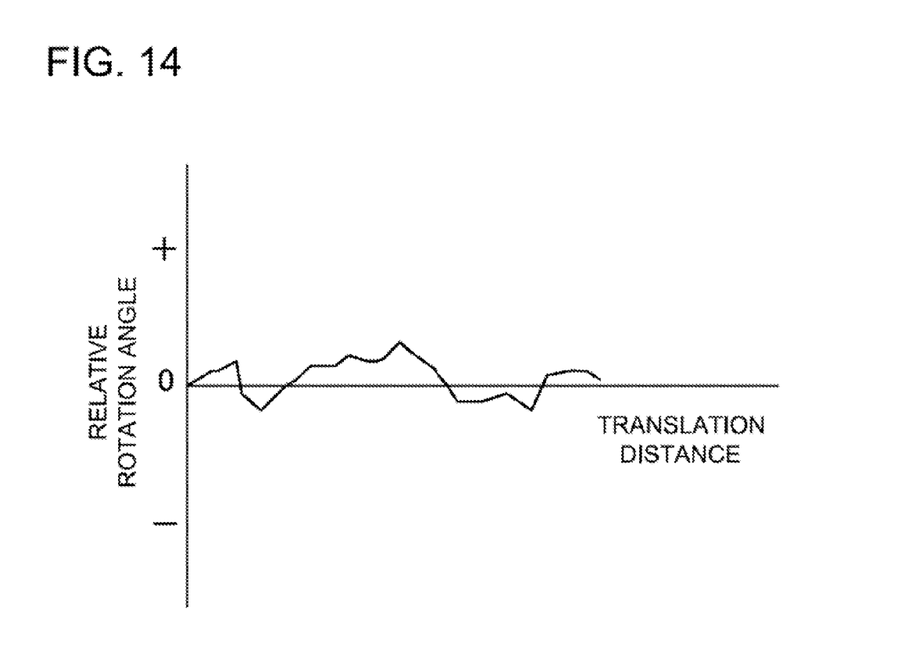
FIG. 14 is a view showing an example of the rotation angle relative to the translation distance, computed by the arithmetic circuit.

When the lower teeth is translated forwardly of the upper teeth, that is, along the X-axis, the arithmetic circuit 31 detects the rotation angle relative to the translation distance along the X-axis, in rotation about the X-axis and Y-axis. FIG. 14 depicts the rotation angle relative to the translation distance along the X-axis, in rotation about the Y-axis. As shown in this drawing, the arithmetic circuit 31 computes the rotation angle relative to the translation distance, and the computation result is displayed on the display monitor 32. FIG. 14 depicts the angle of the lower teeth inclining forwardly and backwardly, with the lower teeth being translated forwardly in a state of contact with the upper teeth. Here, in the dental occlusion, when the lower jaw 12 is moved in the state of dental articulation during excursions from the straight-bitten intercuspal position 33, the rotation of the lower jaw 12 in the direction of a mouth closure is considered to be undesirable; and so a desirable occlusion is judged from FIG. 14.

Further, when the lower teeth is translated laterally of the upper teeth, that is, along the Y-axis, the arithmetic circuit 31 can also compute the rotation angle relative to the translation distance along the Y-axis, in rotation about the X-axis and Y-axis. When the lower teeth is translated along the Y-axis, that is, laterally, and the relative rotation angle in rotation about the X-axis is computed, the angle of the lower teeth inclining laterally can be computed when the lower teeth are translated laterally.

Figure 15:
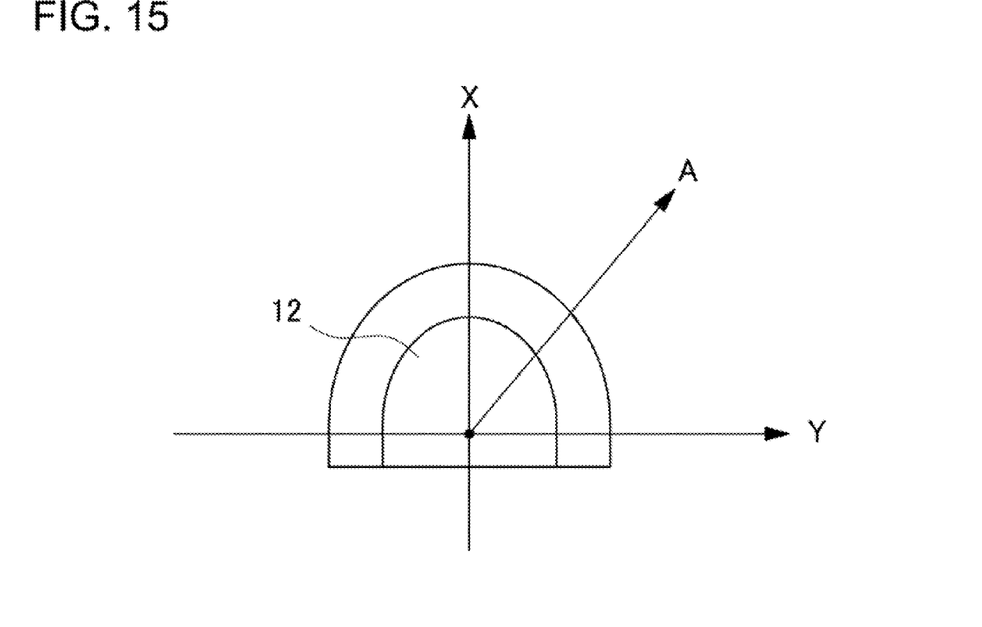
FIG. 15 is a schematic diagram showing the state the lower jaw is translated in an optional direction with respect to the upper jaw.

Further, when the translation distance in an optional direction and the relative rotation angle about an optional axis are detected, the arithmetic circuit 31 can compute the rotation angle relative to the translation distance. For example, FIG. 15 shows the state that the lower jaw 12 is translated diagonally forward as indicated by arrow A, with the lower teeth being in a state of contacting the upper teeth. The arithmetic circuit 31 computes the translation distance in the direction as indicated by arrow A, based on the translation distances along the X-axis and the Y-axis, and also computes the posture relative to the translation distance by detecting the rotation angle relative to the translation distance, in rotation about the X-axis, the Y-axis, and the Z-axis. The arithmetic circuit 31 can also compute the rotation angle about an optional axis, e.g., in rotation about the direction as indicated by the arrow A in the drawing. Thus, in a state of dental occlusion, the posture relative to the translation distance in an optional direction is detected to resultantly judge a desirable occlusion.

Figure 16:
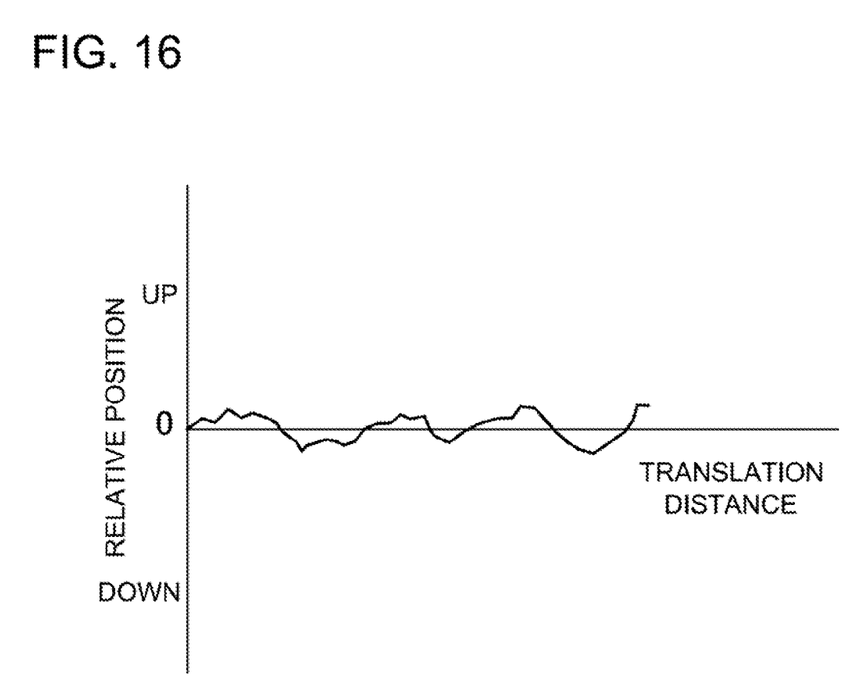
FIG. 16 is a view showing an example of the translation locus with respect to the translation distance, computed by the arithmetic circuit.

Further, in an alternative or in addition to the posture relative to the translation distance, the arithmetic circuit 31 can compute the translation locus of a specific point in the lower jaw 12 with respect to the translation distance in a state of occlusal contact. For example, the arithmetic circuit 31 can also compute the translation locus with respect to the translation distance of the central point on the occlusal plane 34 during excursions. When the lower teeth is translated forwardly of the upper teeth, that is, along the X-axis, this arithmetic circuit 31 computes, as the position along the Y-axis and Z-axis, the translation locus of the specific point with respect to the translation distance along the X-axis. The position along the Z-axis indicates that the lower teeth translates forwardly as well as translating vertically. FIG. 16 indicates the position along the Z-axis relative to the translation distance along the X-axis. The arithmetic circuit 31 computes the position along the Z-axis relative to the translation distance along the X-axis as shown in this drawing, and the computed result is displayed on the display monitor 32. FIG. 16 shows the vertical translation distance of the lower teeth when the lower teeth are translated forwardly in a state of contact with the upper teeth.

Similarly, when the lower teeth is translated laterally of the upper teeth, that is, along the Y-axis, the arithmetic circuit 31 can compute the translation locus of the specific point by detecting the position of the specific point along the Z-axis with respect to the translation distance along the Y-axis. This arithmetic circuit 31 computes the vertical position with respect to the translation distance in the lateral direction, and the vertical position with respect to the lateral translation distance, namely the translation locus is displayed on the display monitor 32.

The arithmetic circuit 31 can also compute the translation locus with respect to the translation distance in an optional direction. For example, as shown in the aforesaid FIG. 15, when the lower jaw 12 is translated diagonally forward as indicated by arrow A in a state that the lower teeth is in contact with the upper teeth, the arithmetic circuit 31 can compute the translation distance in the direction indicated by arrow A, based on the translation distance along the X-axis and the Y-axis, as well as being able to compute the position of the specific point along the Z-axis with respect to the translation distance and compute the translation locus of the specific point. This arithmetic circuit 31 computes a vertical position with respect to the translation distance in an optional direction, and display on the display monitor 32 the vertical position with respect to the translation distance in that direction, namely the translation locus.

The apparatus for measuring the dental occlusion including the arithmetic circuit 31 for detecting both of the posture and rotation locus relative to the translation distance can output to the display monitor 32 both of the posture relative to the translation distance and the translation locus relative to the translation distance, and the display monitor 32 can display both of the relative posture and the translation locus.

The instant apparatus for measuring the jaw movement can be effectively used for a dental prosthesis because the movement of the lower jaw and upper jaw can be accurately detected to measure a dental occlusion or the like.

What is claimed is:

1. An apparatus for measuring a dental occlusion comprising:
- a position sensor configured for detecting a position and posture of a lower jaw relative to an upper jaw;
- an arithmetic circuit configured to compute (a) a posture relative to a translation distance in a state of occlusal contact and (b) to compute a translation locus of a specific point in an occlusal plane with respect to the upper jaw, the translation locus being relative to a translation distance in a state of occlusal contact, and such computations being derived from the position and posture of the lower jaw relative to the upper jaw detected by the position sensor and (c) to compute a rotation angle relative to the translation distance in the state of occlusal contact; and
- a display monitor configured for displaying the posture relative to the translation distance computed by the arithmetic circuit and for displaying the translation locus of the specific point in the occlusal plane with respect to the translation distance computed by the arithmetic circuit and for displaying the rotation angle relative to the translation distance.

2. The apparatus for measuring the dental occlusion as recited in claim 1, wherein the arithmetic circuit computes the translation locus away from an intercuspal position, and the display monitor displays the translation locus away from the intercuspal position.

3. The apparatus for measuring the dental occlusion as recited in claim 1, wherein the position sensor comprises:
- an exciting coil and a sensor coil adapted to be rigidly coupled to regions of the upper and lower jaws, respectively;
- an AC power source adapted to cause AC current to flow to the exciting coil; and
- a detection circuit adapted to detect a position of the lower jaw relative to the upper jaw.

* * * * *